US008481027B2

(12) United States Patent
Stavnsbjerg et al.

(10) Patent No.: US 8,481,027 B2
(45) Date of Patent: *Jul. 9, 2013

(54) FROZEN LACTIC ACID BACTERIAL CULTURE OF INDIVIDUAL PELLET

(75) Inventors: Rikke Stavnsbjerg, Soborg (DK); Inge Knap, Farum (DK); Hans Bisgaard-Frantzen, Rodovre (DK); Borge Windel Kringelum, Ballerup (DK)

(73) Assignee: Chr. Hansen A/S, Horsholm (DK)

( * ) Notice: Subject to any disclaimer, the term of this patent is extended or adjusted under 35 U.S.C. 154(b) by 133 days.

This patent is subject to a terminal disclaimer.

(21) Appl. No.: 12/837,217

(22) Filed: Jul. 15, 2010

(65) Prior Publication Data

US 2011/0008874 A1    Jan. 13, 2011

Related U.S. Application Data

(63) Continuation of application No. 10/590,153, filed as application No. PCT/DK2005/000126 on Feb. 24, 2005, now abandoned, application No. 12/837,217, which is a continuation-in-part of application No. 10/543,240, filed as application No. PCT/DK2004/000025 on Jan. 19, 2004.

(30) Foreign Application Priority Data

Jan. 22, 2003  (EP) .................................. 03001442
Feb. 24, 2004  (EP) .................................. 04100714

(51) Int. Cl.
*A01N 63/00* (2006.01)
*C12N 1/04* (2006.01)
*C12N 1/12* (2006.01)
*C12N 1/20* (2006.01)

(52) U.S. Cl.
USPC ................... 424/93.4; 424/93.45; 435/252.1; 435/252.9; 435/253.4; 435/260

(58) Field of Classification Search
None
See application file for complete search history.

(56) References Cited

U.S. PATENT DOCUMENTS

| | | | | |
|---|---|---|---|---|
| 4,140,800 | A |   | 2/1979 | Kline |
| 4,262,023 | A | * | 4/1981 | Eddy et al. ................... 426/36 |
| 5,637,494 | A |   | 6/1997 | King |
| 5,677,166 | A |   | 10/1997 | Broadbent et al. |
| 5,919,695 | A | * | 7/1999 | Vedamuthu et al. ....... 435/252.5 |
| 2002/0031527 | A1 |   | 3/2002 | Wu et al. |
| 2002/0054936 | A1 | * | 5/2002 | Hoier et al. ................... 426/61 |

FOREIGN PATENT DOCUMENTS

| | | |
|---|---|---|
| DE | 28 05 676 | 2/1978 |
| EP | 0 259 739 | 3/1988 |
| FR | 2 393 251 | 2/1978 |
| WO | WO 00/39281 | 7/2000 |
| WO | WO 2004/065584 | 8/2004 |

OTHER PUBLICATIONS

International Search Report dated Jun. 4, 2004 for PCT Application No. PCT/DK2004/000025.
Non-Final Office Action U.S. Appl. No. 10/543,240 dated Aug. 20, 2008.
Non-Final Office Action U.S. Appl. No. 10/543,240 dated Feb. 18, 2009.
Non-Final Office Action U.S. Appl. No. 10/543,240 dated Nov. 25, 2009.
Non-Final Office Action U.S. Appl. No. 10/543,240 dated Oct. 17, 2011.
Search Report dated Mar. 13, 2003 for EP Application No. 03001442.
Final Office Action U.S. Appl. No. 10/543,240 dated Oct. 13, 2010.
International Search Report PCT/DK2004/000025 dated Mar. 24, 2004.
Paul B. Conrad et al., "Stabilization and Preservation of *Lactobacillus acidophilus* in Saccharide Matrices", Cryobiology, 41, 17-24 (2000).
Fernando Fonseca et al., "Operating Conditions That Affect the Resistance of Lactic Acid Bacteria to Freezing and Frozen Storage", Cryobiology 43, 189-198 (2001).
Yrjo H. Roos, "Phase Transitions in Foods", Food science and technology, Oct. 9, 2002, pp. 99-101.
F.J. Chavarri et al., "Cryoprotective Agents for Frozen Concentrated Starters From Non-Bitter *Streptococcus lactis* Strains", Biotechnology Letters, vol. 10, No. 1, 11-16, (1988).
R. Carcoba et al., "Influence of cryoprotectants on the viability and acidifying activity of frozen and freeze-dried cells of the novel starter strain *Lactococcus lactis* ssp. *Lactis* CECT 5180", Eur Food Res Technol (2000), 211: 433-437.
Food Chemistry Third Edition, edited by Owen R. Fennema, University of Wisconsin—Madison, WI, pp. 55-87, 1996.
International IDS Standard 146A:1998, Yoghurt Identification of Characteristic Microorganisms (*Lactobacillus delbrueckii* Subsp. *Bulgaricus* and *Streptococcus thermophilus*), IDF General Secretariat, Dec. 1997. pp. 1-6.
Yrjo Roos et al., "A Research Note Phase Transitions of Amorphous Sucrose and Frozen Sucrose Solutions", Journal of Food Science, vol. 56, No. 1, 1991, pp. 266-267.
Non-Final Office Action with restriction requirement U.S. Appl. No. 10/590,153 dated Oct. 5, 2009.
Non-Final Office Action U.S. Appl. No. 10/590,153 dated Feb. 18, 2010.

* cited by examiner

*Primary Examiner* — Debbie K Ware
(74) *Attorney, Agent, or Firm* — Foley & Lardner LLP (57) ABSTRACT

A stable, pellet-frozen lactic acid bacteria (LAB) culture comprises at least one additive compound in a commercial relevant package. The pellet-frozen culture has at least 50 g frozen material and a content of viable bacteria of at least $10^9$ colony forming units per gram of frozen material. The individual pellets of the frozen culture do not stick together and remain as individual pellets, when stored at about −46° C., for at least 7 to 14 days.

25 Claims, 2 Drawing Sheets

FROZEN LACTIC ACID BACTERIAL CULTURE OF INDIVIDUAL PELLET

CROSS REFERENCE TO RELATED APPLICATIONS

This application is a continuation of U.S. patent application Ser. No. 10/590,153, filed on Apr. 16, 2007, now abandoned, which is the U.S. national phase of international application PCT/DK2005/000126, filed on Feb. 24, 2005, which claims priority to European Patent Application No. 04100714.7, filed on Feb. 24, 2004. This application also is a continuation-in-part of U.S. patent application Ser. No. 10/543,240, filed on Jan. 8, 2006, which is the U.S. national phase of PCT/DK2004/000025, filed on Jan. 19, 2004, which claims priority to European Patent Application No. 03001442.7, filed on Jan. 22, 2003. The contents of each of these prior applications are incorporated by reference here in their entireties.

FIELD OF THE INVENTION

The present invention relates to a pellet-frozen lactic acid bacteria (LAB) culture in a commercially relevant package that has a weight of at least 50 g frozen material, wherein the frozen material is present in the form of individual pellets characterized by the fact that when stored at a temperature below the initial melting temperature (Tm') of the culture, e.g. at −46° C., for 7-14 days the individual pellets of the frozen culture are not sticking together and therefore substantially remain as individual pellets.

BACKGROUND OF THE INVENTION

Microorganisms are involved in the manufacture of food and feed products including most dairy products. Bacterial cultures, in particular cultures of bacteria that are generally classified as lactic acid bacteria, are essential in the making of all fermented milk products, cheese and butter. Cultures of such bacteria may be referred to as starter cultures and they impart specific features to various dairy products by performing a number of functions.

Dairy starter cultures are generally composed of lactic acid bacteria. In the present context, the expression "lactic acid bacteria" (LAB) designates a group of Gram positive, catalase negative, non-motile, non-sporulating, microaerophilic or anaerobic bacteria which ferment sugars with the production of organic acids, including lactic acid as the predominantly produced acid, formic acid and propionic acid. In the present context lactic acid bacteria comprise of a number of bacterial genera within the phylum *Firmicutes*. The genera *Carnobacterium, Enterococcus, Lactobacillus, Lactococcus, Lactosphaera, Leuconostoc, Melissococcus, Oenococcus, Pediococcus, Streptococcus, Tetragenococcus, Vagococcus* and *Weissella* are recognized as LAB. Also lactic acid-producing Gram-positive bacteria belonging to the phylum *Actinobacteria* such as the genera *Aerococcus, Microbacterium* and *Propionibacterium* as well as *Bifidobacterium* are in the present context considered as LAB. The industrially most useful lactic acid bacteria are found among *Lactococcus* species, *Streptococcus* species, *Enterococcus* species, *Lactobacillus* species, *Leuconostoc* species, *Bifidobacterium* species and *Pediococcus* species.

In addition to the their use in the dairy industry lactic acid bacteria cultures also find widely use in the meat processing industry as well as a number of other industries.

Commercial starter cultures may be distributed as frozen cultures. Highly concentrated frozen cultures are commercially very interesting since such cultures can be inoculated directly into the fermentation medium (e.g. milk or meat) without intermediate transfer. In others words, such highly concentrated frozen cultures comprise bacteria in an amount that makes in-house bulk starter cultures at the end-users superfluous. A "bulk starter" is defined herein as a starter culture propagated at the food processing plant for inoculation into the fermentation medium. Highly concentrated cultures may be referred to as direct vat set (DVS)-cultures. In order to comprise sufficient bacteria to be used as a DVS-culture at the end-users, a concentrated frozen culture generally has to have a weight of at least 50 g and a content of viable bacteria of at least 109 colony forming units (CFU) per g.

An important issue in the practical use of frozen cultures is the convenience of the actual handling of the cultures. Whereas cultures frozen "on block" are difficult to handle it has been found that cultures frozen in pellets are very easy to handle both for the producer and the consumer.

Consequently, a thriving market for highly concentrated pellet frozen cultures—so-called frozen direct vat set (F-DVS)-cultures—has formed.

A number of publications concerned with the viability of frozen cultures have occurred.

Chavarri et al. (1988) describes that the viability of a frozen pure Streptococcus lactis culture can be improved by addition of 5% lactose or 5% sucrose.

Cárcoba et al. (2000) describes that the viability of a frozen pure *Lactococcus lactis* subsp. *lactis* culture can be improved by addition of different cryoprotective agents such as sugars (lactose, sucrose and trehalose), glutamic acid and gelatin.

U.S. Pat. No. 4,140,800 (Kline), describes that the viability of freeze-dried cultures can be improved by addition of different cryoprotective agents. Also the viability of frozen cultures added lactose, sucrose or maltose are discussed.

WO00/39281 (Kringelum et. al.) describes that the viability of a non-frozen, liquid starter culture can be improved by addition of different cryoprotective agents, and

SUMMARY OF THE INVENTION

Commercially, a pellet-frozen lactic acid bacteria (LAB) culture is normally provided in a suitable package (e.g. in a 2 L tetra pack of carton). It is normally stored at a storage temperature of around −46° C. and the frozen material is present in the form of individual pellets of a relatively small weight.

Prior to the present invention, the present inventors believed that there were no significant problems with respect to storage of such commercial relevant pellet-frozen lactic acid bacteria (LAB) cultures.

However, based on different studies the present inventors identified that when a number of commercially relevant cultures where stored approximately at −46° C. for 7 days or longer the individual pellets were sticking together and making larger clumps. In the industrial setting the clumping create handling problems. It is e.g. significantly more difficult to administer an adequate dose from the culture package when the culture is clumped. It may even be difficult to get the clumped culture out of the package in a convenient way.

Further studies identified that the "problematic" cultures could be characterized by having a Tm' value (onset of ice melting, as defined by Roos (1995)) of the pellet-frozen lactic acid bacteria (LAB) culture below the storage temperature of approximately −46° C. The Tm' value is a standard physical chemistry term used in the food industry and elsewhere. Tm' is routinely measured by Differential Scanning Caloriometry (DSC) techniques as described by Roos (1991). It relates to the onset temperature of melting of the food product (here the frozen LAB culture). For further details reference are made to the textbooks "Food Chemistry" Fennema (1996) and "Phase Transition in Foods" Roos (1995).

Without being limited to theory, it is believed that when a frozen culture has a Tm' value below its storage temperature, e.g. approximately −46° C., an initial phase transition (melting) occur and cause the individual pellets to stick together and form larger clumps.

In summary, the work of the present inventors has identified hitherto unrecognized storage problems in relation to the physical appearance of some types of commercially relevant highly concentrated pellet-frozen lactic acid bacteria cultures. Once having identified this problem, the present inventors could start to trying solve the problem.

Independent of any possible theoretical explanation, the present inventors identified that by adding certain relevant additive compounds to a problematic pellet-frozen culture, one could obtain a pellet-frozen culture, which after 7 to 14 days of storage at −46° C. did not form clumps of individual pellets. Such cultures were characterized by that the individual pellets of the frozen culture were not sticking together and therefore substantially remain as individual pellets even after prolonged storage at approximately −46° C.

Overall, the relevant additive compounds may be characterized by that they are able to increase the Tm' value, of the frozen culture, to a value above the storage temperature, e.g. —46° C. such as for instance to raise the Tm' value from range −70 to −46° C. to the range from −45 to −15° C.

The working examples herein describe preferred examples of suitable additive compounds. Described compounds include trehalose, maltodextrin, cyclodextrin, spray gum, fish gelatin bloom and maltitol. Based on common general knowledge the skilled person is perfectly capable of identifying further relevant additive compounds that are able to increase the Tm' value, of a frozen culture, to a value above the storage temperature, e.g. −46° C.

As said above, in order to comprise sufficient bacteria a commercially relevant highly concentrated frozen culture generally has a weight of at least 50 g and a content of viable bacteria of at least $10^9$ colony forming units (CFU) per g. The cultures described in the articles of Chavarri (1988) and Carcoba (2000) are not directed to the physical stability of pellet-frozen cultures, but rather to the viability of the frozen bacteria in the present context not considered commercially relevant highly concentrated frozen cultures since they are made on much smaller scale and comprise significantly less grams of frozen culture, and moreover the described cultures are not pellet-frozen cultures. Also, the cultures described by Chavarri (1988) and Carcoba (2000) are not directed to the physical stability of pellet-frozen cultures at all, but rather to the viability of the frozen bacteria.

Accordingly, a first aspect of the invention relates to a pellet-frozen lactic acid bacteria (LAB) culture, typically in a commercially relevant package, that has a weight of at least 50 g frozen material. The frozen material is present in the form of individual pellets, having a content of viable bacteria of at least $10^9$ colony forming units (CFU) per g frozen material and comprising from 0.5% to 13% of an additive compound measured as w/w of the frozen material.

The additive compound is selected from the group of compounds that, by using an amount of 10% of the additive compound measured as w/w of the frozen material, are able to increase the Tm' (onset temperature of ice melting) of the frozen lactic acid bacteria (LAB) culture, which without the additive compound has a Tm' value from −70° C. to −46° C., to a Tm' value from −45 to −15° C. (measured by DSC).

Furthermore, the frozen lactic acid bacteria (LAB) culture is characterized by that when stored at approximately −46° C. for 7-14 days the individual pellets of the frozen culture are not sticking together and therefore substantially remain as individual pellets where this is measured by following test:

The individual pellets of the frozen culture are pellet frozen in liquid nitrogen and 100 individual pellets (around 5-100 g of pellets) are poured into a petridish, thus forming a thin layer of loose, individual single pellets, the layer being characterized in that the majority of the pellets are in physical contact with one or more of its neighbor pellets, placed at approximately −46° C. for 7-14 days and examined to see if the pellets are still loose or if the pellets had made clumps or are sticking together, wherein the criteria for the individual pellets of the frozen culture substantially remaining as individual pellets are that at least 80 of the 100 individual pellets remain as loose individual single pellets.

With respect to the frozen culture of the present invention, the additive compound should preferably be added to the viable bacteria before they are frozen.

Accordingly, in a second aspect the invention relates to a method for making a pellet-frozen lactic acid bacteria (LAB) culture of the first aspect of the invention and embodiments as described herein, comprising following steps:
(i) adding an additive compound to viable bacteria to get at least 50 g of material with a content of viable bacteria of at least $10^9$ colony forming units (CFU) per g material and comprising the additive compound in an amount from 0.5% to 13% measured as w/w of the material,
(ii) freezing the material to get pellet-frozen material, and
(iii) packing the frozen material in a suitable way to get a packed pellet-frozen lactic acid bacteria (LAB) culture of the first aspect of the invention and embodiments as described herein.

A third aspect of the invention relates to a pellet-frozen lactic acid bacteria (LAB) culture obtainable by the method for making a pellet-frozen lactic acid bacteria (LAB) culture of the second aspects of the invention.

A fourth aspect of the invention relates to use of the pellet-frozen lactic acid bacteria (LAB) culture as described above in a process for making a food or feed product.

DEFINITIONS

Prior to a discussion of the detailed embodiments of the invention a definition of specific terms related to the main aspects of the invention is provided.

The term "LAB that are able to utilize sucrose" denotes LAB that are able to ferment the sugar sucrose with the production of acids. This is the same definition as in PCT publication number WO 2004/065584 A1.

The term "material" of the culture denotes the relevant substances of the culture including both the viable bacteria and the additive compound. Possible packing is not included. Consequently, the weight of the material of the culture does not include the weight of possible packing.

The term "packing" or "package" should be understood broadly. It denotes that the pellet-frozen lactic acid bacteria (LAB) culture should be packed in order to be provided to the user. It may be packed in a bottle, a tetra-pack© container, etc.

The term "an additive compound" may in the present context be a single specific additive compound or it may be two or more different additive compounds. Accordingly, the w/w percentage of the additive compound(s) within the culture material should be understood as the sum of the amount of additive compound(s). Preferably, the term relates to a compound that is added to the culture after fermentation. Accordingly, it may be a compound that is not present in a significant amount in the culture fermentation broth as such.

The terms "pellet-frozen" and "pellet-frozen culture" refer to a culture frozen by use of a method which results in pellets or granula of the frozen culture. A pellet-frozen culture may conveniently be made by adding the culture dropwise into liquid $N_2$ forming frozen pellets or granula of the culture. Typically, but not necessarily, the process is performed on trays in a conventional industrial freeze-drying plant.

The term "pellets" or "granula" refers to small solid entities formed by frozen liquid of an average size between 0.1 and 10 mm.

Embodiments of the present invention is described below, by way of examples only

DETAILED DESCRIPTION OF THE INVENTION

Tm' Value

As explained above, the Tm' value is a standard known term in physical chemistry describing the temperature at which the onset of ice melting occurs. In the present context Tm' denotes the temperature at which the onset melting of a frozen LAB culture occurs.

Preferably, the Tm' value is measured by use of the DSC protocol described in the section named "Measurement of Tm'" of working example 1 herein.
Pellet Clumping Test As explained with respect to the first aspect of the invention the test to analyze if the pellet-frozen lactic acid bacteria (LAB) culture is a culture that may be characterized by that when stored at approximately −46° C. (in the present situation a freezer preset to −50° C. had an sample temperature of −46° C.) for 7-14 days the individual pellets of the frozen culture are not sticking together and therefore substantially remain as individual pellets in a test comprising following:

The individual pellets of the frozen culture are pellet frozen in liquid nitrogen and 100 individual pellets (around 5-100 g of pellets) are poured into a petridish, thus forming a thin layer of loose individual single pellets, the layer being characterized in that the majority of the pellets are in physically contact with one or more of its neighbor pellets, placed at approximately −46° C. for 7-14 days and examined to see if the pellets are still loose or if the pellets had made clumps or are sticking together, wherein the criteria for that the individual pellets of the frozen culture substantially remain as individual pellets are that at least 80 of the 100 individual pellets remain as loose individual single pellets. More preferably at least 90 of the 100 individual pellets remain as loose individual single pellets and even more preferably at least 95 of the 100 individual pellets remain as loose individual single pellets.

Examining and counting individual pellets that remain as loose individual single pellets may be done visually. It is within the skilled person capacity to do this in a consistent way where the results would, within normal limited technical uncertainty, be consistent and repeatable. Working example 1 herein provides further technical details.
A Pellet-Frozen Lactic Acid Bacteria (LAB) Culture Preferably, the term "a frozen lactic acid bacteria (LAB) culture" denotes herein a culture which without comprising the added additive compound as described herein has a Tm' value of from −70° C. to −46° C. The culture may be frozen in the form of pellets or granula, forming a "a pellet-frozen lactic acid bacteria (LAB) culture". A pellet-frozen lactic acid bacteria (LAB) culture may conveniently be made by adding the culture dropwise into liquid N2 forming frozen pellets or granula of the culture.

The LAB of the culture may be any in particular commercial relevant LAB that do not utilize sucrose according to International IDE Standard 146A:1998 "Identification of Characteristic Microorganisms" by use of appropriate API test kits (bioM6rieux SA, Lyon, France). API kit "rapid ID 32 STREP" and "50 CHL Medium" is used to establish the sucrose utilization status for most LAB genera.

Preferably, the LAB is a LAB selected from the group comprising *Bifidobacterium* spp., *Brevibacterium* spp., *Propionibacterium* spp., *Lactococcus* spp. including *Lactococcus lactis* subsp. *lactis* and *Lactococcus lactis* subsp. *cremoris*, *Lactobacillus* spp. including *Lactobacillus acidophilus*, *Streptococcus* spp., *Enterococcus* spp., *Pediococcus* spp., *Leuconostoc* spp., *Oenococcus* spp. and fungal spp. including *Pencillium* spp., *Cryptococcus* spp., *Debraryomyces* spp., *Klyveromyces* spp. and *Saccharomyces* spp.

Even though some of these species in general are described as capable of utilizing sucrose mutants that are not able to utilize sucrose, have been, and will continuously be isolated. No matter how such mutations are isolated or obtained, they are still an aspect of the present invention.

The industrially most useful lactic acid bacteria are found among *Lactococcus* species, *Streptococcus* species, *Enterococcus* species, *Lactobacillus* species, *Leuconostoc* species and *Pediococcus* species.

The term "mixed lactic acid bacteria (LAB) culture" denotes a mixed culture that comprises two or more different LAB species. The term a "pure lactic acid bacteria (LAB) culture" denotes a pure culture that comprises only a single LAB species specie.

The culture as described herein may be a mesophilic culture consisting of mesophilic bacteria having optimum growth temperatures at about 30° C. A "a mesophilic culture" is a culture that comprises two or more different mesophilic LAB species.

Typical organisms belonging to the mesophilic group include *Lactococcus lactis* subsp. *lactis*, *Lactococcus lactis* subsp. *cremoris*, *Leuconostoc mesenteroides* subsp. *cremoris*, *Pediococcus pentosaceus*, *Lactococcus lactis* subsp. *lactis* biovar. *diacetylactis* and *Lactobacillus casei* subsp. *casei*. Thermophilic lactic acid bacterial species include as examples *Streptococcus thermophilus*, *Enterococcus faecium*, *Lactobacillus lactis*, *Lactobacillus helveticus*, *Lactobacillus delbrueckii* subsp. *bulgaricus* and *Lactobacillus acidophilus*.

The culture as described herein may comprise LAB that are not able to utilize sucrose. An so-called O-culture is used to make cheese without holes (Cheddar, Cheshire, Feta) and typically comprises one or more organisms selected from the group comprising *Lactococcus lactis* subsp. *lactis* and *Lactococcus lactis* subsp. *cremoris*. In general O-cultures are considered not to utilize sucrose.

Highly Concentrated Pellet-Frozen Lactic Acid Bacteria Cultures

The frozen cultures as described herein are what in the food industry may be termed highly concentrated pellet-frozen lactic acid bacteria cultures. In order to comprise sufficient bacteria, such cultures should be relatively big (have a sufficient weight) combined with a relatively high concentration of viable bacteria. It is obvious that if relatively more bacteria is required, the weight and/or the concentration of viable bacteria should be increased.

Preferably, a pellet-frozen lactic acid bacteria (LAB) culture as described herein has a weight of at least 100 g frozen material, more preferably a weight of at least 250 g frozen material, even more preferably a weight of at least 500 g frozen material and most preferably a weight of at least 900 g frozen material. Preferably, the weight of the frozen material is less than 500 kg.

Preferably, a pellet-frozen lactic acid bacteria (LAB) culture as described herein has a content of viable bacteria of at least $5 \times 10^9$ colony forming units (CFU) per g frozen material, more preferably a content of viable bacteria of at least $10^{10}$ colony forming units (CFU) per g frozen material, and most preferably a content of viable bacteria of at least $2 \times 10^{10}$ colony forming units (CFU) per g frozen material.

Fermentation and suitable fermentation media for LAB are known in the art and the skilled person is capable of selecting a suitable media and fermentation conditions in relation to the specific LAB. Suitable media and fermentations are given in the working example section herein.

In order to get sufficient amount of bacteria, it is in the present context preferred to make a relatively large-scale fermentation in suitable big fermentation tanks. Fermentation tanks of at least 50 L, preferably at least 90 L, even more preferably 500 L or bigger are preferred.

After a suitable fermentation, the viable bacteria are preferably isolated by removal of the liquid (supernatant) of the fermentation media (e.g. by centrifugation). The isolated viable bacteria may be termed the isolated biomass. The isolated viable bacteria shall preferably have a content of viable bacteria of at least $10^9$ colony forming units (CFU) per g frozen material, more preferably a content of at least $5 \times 10^9$ CFU per g frozen material, and most preferably a content of at least $10^{10}$ CFU per g frozen material.

After addition of the additive compound (see below) to the concentrated culture. The culture may conveniently be frozen by adding the mixture dropwise into liquid N2 forming frozen pellets or granula of the mixture. A feasible method for the freezing process is described in DE2805676 and FR2393251.

The pellet-frozen culture is then packaged a suitable way in order to be provided to the user.

Additive Compound

As discussed above, preferably the relevant additive compounds are characterized by that they are able to increase the Tm' value, of the frozen culture, to a value above the storage temperature, e.g. $-46°$ C., such as to a Tm' value from $-45°$ C. to $-15°$ C., more preferably to a Tm' value from $-43°$ C. to $-15°$ C. and even more preferably to a Tm' value from $-39°$ C. to $-15°$ C.

Working example 2 herein illustrates a rapid experimental strategy to identify relevant additive compounds. To a "model" frozen culture with a Tm' value below $-46°$ C. (in example 2 "model" culture has a Tm' value of $-54°$ C.) was added different relevant compounds (10% W/W) and the Tm' values before and after addition were measured by DSC.

The "model" culture of example 2 and the test protocol of this example 2 is preferably used to evaluate if specific additive compounds of interest may be characterized by that they are able to increase the Tm' value, of the frozen culture, to a value above the $-46°$ C. such as to a Tm' value from $-45°$ C. to $-15°$ C., more preferably to a Tm' value from $-43°$ C. to $-15°$ C., even more preferably to a Tm' value from $-39°$ C. to $-15°$ C.

In working example 2 it can be seen that Cyclodextrin increased Tm' to $-44°$ C., Maltitol increased Tm' to $-42°$ C., Trehalose increased Tm' to $-38°$ C., Fish gelatin increased Tm' to $-37°$ C., Maltodextrine increased Tm' to $-32°$ C. and Spraygum increased Tm' to $-31°$ C.

Preferably, the additive compound is a compound with a molecular weight (MW) from 150 to 100000 g/mol, more preferably 250 to 100000 g/mol, even more preferably from 300 to 40000 g/mol and most preferably from 500 to 15000 g/mol.

In a preferred embodiment, the additive compound is an additive compound selected from the group consisting of Cyclodextrin, Maltitol, Fish gelatin, Maltodextrine (preferably maltodextrine DE 2 to maltodextrine DE 19), Spraygum (e.g. Spraygum IRX 51693), inosine-5'-monophosphate (IMP) and inosine.

The frozen culture comprises of 0.5% to 13% of an additive compound measured as w/w of the frozen material, preferably from 1% to 12% of an additive compound measured as w/w of the frozen material, more preferably from 2% to 10% of an additive compound measured as w/w of the frozen material and even more preferably from 5% to 10% of an additive compound measured as w/w of the frozen material.

In a more preferred embodiment the additive compound is also a cryoprotective agent. At the amount disclosed above, the additive compound not only prevents the individual frozen pellets from clumping together but also functions as a cryoprotective agent to increase viability of the bacteria culture during storage at a low temperature. As such, no additional cryoprotective agent is required for viability of the bacteria culture.

The addition of the additive compound to the isolated viable bacteria (biomass) may be done by mixing solid additive compound with the biomass for e.g. 30 minutes at a suitable temperature. If the additive compound agent is e.g. maltodextrin a suitable temperature may be room temperature. Alternatively, a sterile solution of the additive compound may be mixed with the biomass.

Cryoprotective Agent

The pellet-frozen culture of the invention may additionally comprise a cryoprotective agent to increase viability of the bacteria culture. The term "a cryoprotective agent" denotes a substance that is able to improve the storage stability of the frozen culture measured by viability of the culture. In the present context it may be a single specific cryoprotective agent or it may be two or more different agents. Accordingly, the w/w percentage of the cryoprotective agent(s) within the culture material should be understood as the sum of the amount of cryoprotective agent(s).

The cryoprotective agent may preferably be selected from proteins or protein hydrolysates. Preferred suitable examples of these include the ones selected from the group consisting of Malt extract, Skimmed milk powder, Whey powder, Yeast extract, Gluten, Collagen. Gelatin, Elastin, Keratin, and Albumins.

More preferably, the cryoprotective agent is a carbonhydrate or a compound involved in bio-synthesis of nucleic acids. Preferred suitable carbonhydrates include the ones selected from the group consisting of Pentoses (eg. Ribose, Xylose). Hexoses (eg. fructose, mannose, Sorbose), Disaccharides (eg. Sucrose, Trehalose, Melibiose, Lactulose), Oligosaccharides (eg. Raffinose), Oligofrutoses (eg. Actilight, Fribroloses), Polysaccharides (eg. Maltodextrins, Xanthan Gum, Pectin, Alginate, Microcrystalline cellulose, Dextran, PEG), and Sugar alcohols (Sorbitol, Manitol). Most preferably, the carbonhydrate is a carbonhydrate with a molecular weight (MW) from 150 to 100000 g/mol, more preferably 250 to 100000 g/mol, even more preferably from 300 to 40000 g/mol and most preferably from 500 to 15000 g/mol.

A Method for Making a Pellet-Frozen Lactic Acid Bacteria (LAB) Culture

As said above, a second aspect of the invention relates to a method for making a pellet-frozen lactic acid bacteria (LAB) culture of the first aspect of the invention comprising following steps:

(i) adding an additive compound to viable bacteria to get at least 50 g of material with a content of viable bacteria of at least $10^9$ colony forming units (CFU) per g material and comprising the additive compound in an amount from 0.5% to 13% measured as w/w of the material, (ii) freezing the material to get pellet-frozen material, and (iii) packing the pellet-frozen material in a suitable way.

As discussed above, the herein most relevant "problematic" cultures are pellet-frozen lactic acid bacteria (LAB) cultures, which without comprising the added additive compound as described herein has a Tm' value of from −70° C. to −46° C.

Accordingly, in a preferred embodiment before making the addition of the additive compound according to step (i) above one has measured the Tm' value of the frozen lactic acid bacteria (LAB) culture without comprising the additive compound and identified that it has a Tm' value of from −70° C. to −46° C. or even lower.

Before making the addition of the additive compound according to step (i) above one has performed a pellet clumping test (see above) and identified that the individual pellets of the frozen culture stick together at storage at −46° C.

Preferably, after the addition of the additive compound the Tm' value of the frozen lactic acid bacteria (LAB) culture comprising the additive compound is measured and it is verified that the Tm' value is above −46° C., preferably from −45° C. to −15° C., more preferably from −43° C. to −15° C. and even more preferably from −39° C. to −15° C.

Finally, after the addition of the additive compound the culture is pellet-frozen and a pellet clumping test (see above) ensuring that at least 80 of the 100 individual pellets remain as loose, individual single pellets, is performed.

Use of the Frozen Lactic Acid Bacteria (LAB) Culture

A frozen lactic acid bacteria (LAB) culture as described herein may be used in a process for making a food or feed product according to the art.

EXAMPLES

Example 1

R604-E (a commercially available frozen O-culture, Chr. Hansen A/S, Denmark) tends to form sticky pellets during frozen storage. In the present study this problem is approached by taking a closer look at the melting temperature, and trying to increase it by adding caseinate, sucrose or maltodextrin.

Aim:

To evaluate if it is possible to raise the melting point of F-DVS of R604-E by using additives. The effect of using additives to increase the melting point of R604-E is evaluated:
visually, and
by measuring the Tm' by DSC for each of the tested formulations.

i) Material:

2 kilos of commercially available culture, F-DVS R 604-E (Chr. Hansen A/S, Hoersholm, Denmark, Batch 2441258, material no. 616581).

(ii) Additives Solution Used for Formulation to Raise the Melting Point:

50% (w/w) sucrose solution (Danisco, Denmark).
10% (w/w) Na-caseinate solution (Aria, Denmark).
30% (w/w) Malto Dextrin DE 10 solution (Glucidex 10, Roquette Freres, Lestrem, France).
30% (w/w) Malto Dextrin DE 2 solution (Glucidex 2, Roquette Freres, Lestrem, France).

iii) Recipe for formulation of F-DVS R604-E:

The frozen concentrate was thawed and mixed with additives according to Table 1.

TABLE 1

Formulations of R604-E

| Formulation ID | Amount cell concentrate (g) | Additives (g) | Dilution of conc. x | Additives* (%) |
|---|---|---|---|---|
| F-DVS R604E/Reference | 300 | 0 | 1 | 0 |
| F-DVS R604E/6% Sucrose | 300 | 41 | 1.14 | 6 |
| F-DVS R604E/10% Sucrose | 300 | 75 | 1.25 | 10 |
| F-DVS R604E/6% Malto Dextrin DE 10 | 300 | 75 | 1.25 | 6 |
| F-DVS R604E/6% Malto Dextrin DE 2 | 300 | 75 | 1.25 | 6 |
| F-DVS R604E/2% Na-caseinate | 300 | 75 | 1.25 | 2 |

*g dry matter additive/g concentrate

Visual Evaluation of Melting Point of F-DVS R604.

The 6 formulations of F-DVS R-604 E were pellet-frozen in liquid nitrogen and 100 individual pellets (around 20-30 g) of pellets were poured into petridishes, thus forming a thin layer of loose, single pellets.

One sample of each of the formulations was placed in a freezer preset to at −50° C., the actual temperature of the samples was −46° C. After 7 days of storage the samples were examined to see if they were still loose or if the pellets had made clumps or seemed sticky—and if so—their willingness to be shaken into loose particles again.

TABLE 2

Visual inspection of frozen pellets and measured Tm'

| Sample marked: | | Stored at −46° C. | Tm' measured in samples stored at −46° C., 6 days |
|---|---|---|---|
| F-DVS R604-E Reference | Batch 2441258 | − | −56 |
| F-DVS R604-E 6% Sucrose | Batch 2441258 | − | −49 |
| F-DVS R604-E 10% Sucrose | Batch 2441258 | ++ | −42 |
| F-DVS R604-E 6% Malto Dextrin DE 10 | Batch 2441258 | +++ | −44 |

TABLE 2-continued

Visual inspection of frozen pellets and measured Tm'

| Sample marked: | | Stored at −46° C. | Tm' measured in samples stored at −46° C., 6 days |
|---|---|---|---|
| F-DVS R604-E 6% Malto Dextrin DE 2 | Batch 2441258 | +++ | −42 |
| F-DVS R604-E 2% Na-caseinate | Batch 2441258 | − | −58 |

− = Clump, caked or sticky. (less than 20 of the 100 individual pellets remain as loose individual single pellets)
+ = Partly loose particles. (less than 60 of the 100 individual pellets remain as loose individual single pellets)
++ = Nearly loose particles. (at least 80 of the 100 individual pellets remain as loose individual single pellets)
+++ = Loose particles (at least 90 of the 100 individual pellets remain as loose individual single pellets)

Measurement of Tm':

The samples were prepared in 100 µL alumina crucibles and frozen in liquid nitrogen. One sample of each of the formulations and F-DVS R604 was placed for 6 days at −46° C.

The phase transition was measured on a Mettler Toledo 822e Differential Scanning Calorimeter (a DSC) with 100 µL, alumina crucibles, temperature program, insert temp −90° C., scanning temp. program: 5° C./min. −130° C.-0° C. The Tm' values (onset of ice melting, as defined by Roos (1995)) were measured. Results are shown in table 2.

We observe that use of >6% sucrose and 6% maltodextrin (2 or 10) increase the Tm' value of frozen pellets. It is not possible to see any effect of Na-caseinate. From the visual inspection 10% sucrose and the two different maltodextrin show positive effect against the tendency to make sticky pellets.

Example 2

Aim

To identify what kind of additives that could increase the melting point of frozen culture a screening study was made. The following additives were tested:
Trehalose, Malto dextrin 12, cyclo dextrin, spray gum, PEG, Fish gelatin, maltitol, Sodium chloride, glycerol.
i) Material:
F-DVS R 604-E (Batch 2471755, material 616581) for details please see Example 1.
ii) Additives Solution Used for Formulation to Raise the Melting Point:
50% (w/w) trehalose.
30% (w/w) Malto Dextrin DE 12 (Glucidex 12, Roquette Freres, Lestrem, France). 30% (w/w) cyclodextrin
30% (w/w) Spray gum (I X 51693 from CNI)
30% (w/w) PEG (PEG 6000, Merck, Germany)
30% (w/w) Fish gelatin bloom 200 (SKW Biosystems, France)
30% (w/w) maltitol
30% (w/w). Sodium Chloride
30% (w/w) Glycerol
iii) Recipe for Formulation of F-DVS R604-E:
The frozen F-DVS R604-E concentrate was thawed and mixed with the different additives to a final formulation of 10% (W/W).
Measurement of Tm':
The samples were prepared in 100 µL alumina crucibles and frozen in liquid nitrogen. The phase transition curves were recorded on the Mettler Toledo 822e Differential Scanning Calorimeter for the 9 formulations and compared to the reference sample (R604E without additives). The samples were inserted to the DSC at −90° C. and run using temperature program: insert temperature −90° C.; temperature scanning 7° C./min from −130° C. to 0° C.
Result:
The phase transition curves were made and the Tm' values determined as described by Roos (1991) the values are given in table 3 below:

TABLE 3

| Observed Tm' (° C.). | |
|---|---|
| Additive | Tm' (° C.) |
| Trehalose | −38 |
| Malto Dextrin DE 12 | −32 |
| Cyclodextrin | −44 |
| Spray gum (IRX 51693) | −31 |
| PEG 6000 | −52 |
| Fish gelatin bloom 200 | −37 |
| Maltitol | −42 |
| Sodium Chloride | −62 |
| Glycerol | −54 |
| Culture, R-604 E | −54 |

The Tm' for the reference sample is found to be −54° C. (onset of ice melting).
The following additives are increasing Tm':
PEG (−53° C.),
Cyclodextrin (−44° C.),
Maltitol (−42° C.),
Trehalose (−38° C.)
Fish gelatin (−37° C.)
Maltodextrine 12 (−32° C.)
Spray gum (−31° C.)
Glycerol and sodium chloride did not increase the melting point of frozen culture pellets.

Example 3

In this trial the intension was to evaluate the relationship between amount of additive and the increase in Tm' measured on DSC.
i) Material:
F-DVS CH N 19 (Batch 2421868) (commercially available frozen LD-cultures, Chr. Hansen A/S, Denmark).

TABLE 4

| Formulation CII N19 using sucrose and trehalose as additive agents. | | | | |
|---|---|---|---|---|
| Formulation ID | cell concentrate (g) | 50% Sucrose (g) | Dilution of conc X | Sucrose % |
| F-DVS/-additives (Reference) | 300 | 0.00 | 1.00 | 0.00 |
| F-DVS/5% Trehalose | 300 | 43.00 | 1.14 | 4.99 |
| F-DVS/3% Sucrose | 300 | 19.00 | 1.06 | 2.98 |
| F-DVS/5% Sucrose | 300 | 34.00 | 1.11 | 5.09 |
| F-DVS/6% Sucrose | 300 | 42.00 | 1.14 | 6.14 |
| F-DVS/8% Sucrose | 300 | 57.00 | 1.19 | 7.98 |
| F-DVS/9% Sucrose | 300 | 66.00 | 1.22 | 9.02 |
| F-DVS/10% Sucrose | 300 | 75.00 | 1.25 | 10.00 |
| F-DVS/13% Sucrose | 300 | 105.00 | 1.35 | 12.96 | ii) Additive Solutions Used for Formulation to Raise The Melting Point:
The concentration of sucrose per gram biomass varied from 3% (w/w) up to 13% (w/w). Trehalose was only tested on a 5% (w/w) level. All sucrose concentrations were prepared from a 50% (w/w) sucrose solution added to the biomass. The trehalose concentration was prepared from a 40% (w/w) solution.

Measurement of Tm':

The frozen F-DVS R604-E concentrate was thawed and mixed with the different additives as indicated in table 4. Then samples were transferred to 100 µL alumina crucibles and frozen in liquid nitrogen and stored at −46° C. before analyzed. The phase transition curves were recorded on the DSC for the 8 formulations and compared to the reference sample (R604E without additives). The samples were inserted into the DSC at −90° C. and run using temperature program: insert temperature −90° C.; temperature scanning: 5° C./min. −130° C.-0° C.

From these phase transition curves the Tm'. The correlation between Tm' and amount of disaccarides added can be seen in FIG. 1.

Figure 1:
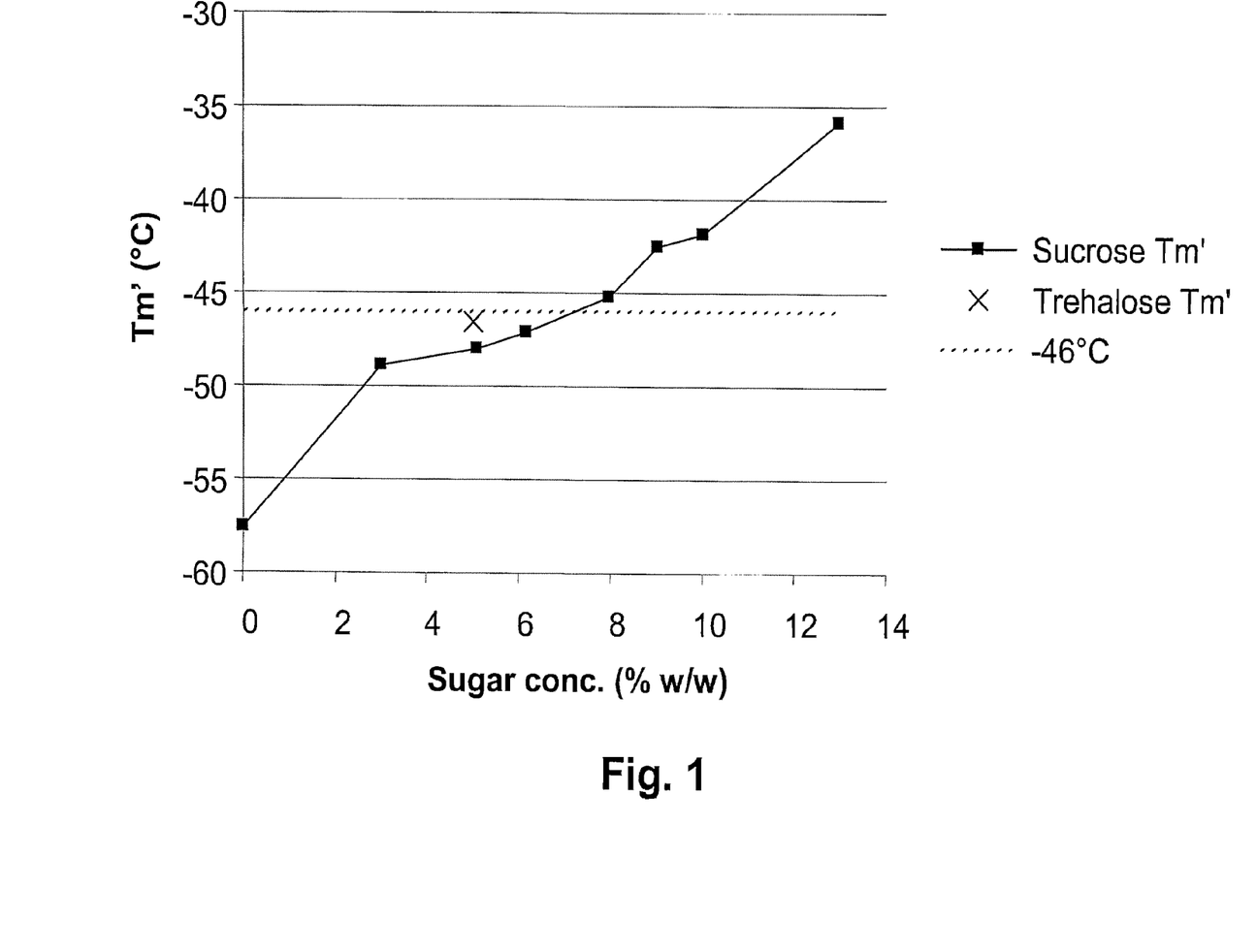
FIG. 1: The correlation between the temperature at which the onset of ice melting occurs, Tm', and amount of disaccarides added can be seen in this figure. For further details, see working Example 3. The storage temperature, −46° C., is indicated by a punctured line.

From FIG. 1 it can be seen that 8% sucrose and more will ensure that the frozen culture do not start melting at −46° C. storage.

Example 4

Commercially available cultures from Chr. Hansen A/S, Denmark (HP, BPS, HP-1, LP, LL-2) were analyzed for initial melting point before and after addition of maltodextrin (Glucidex 12 from Roquette Freres, Lestrem, France). The products are sold as frozen pellets, and these should be kept loose which is secured by an initial melting point above the storage temperature.

Aim:

The aim of the present study was to raise the initial melting point above storage temperature in order to obtain loose pellets.

Materials and Methods:

i) Materials

Glucidex 12 (Roquette Freres, Lestrem, France) was used as additive compound.

100 g of each of the cultures listed in Table 5 was used. B indicates that glycerine was not added to the culture, where as A indicates that 10% v/v glycerine has been added before pellet freezing.

TABLE 5

Cultures used

| Material no. | Product | Batch no. |
|---|---|---|
| 73258 | BP A/B | 2511924 |
| 73264 | BPS A | 2511063 |
| 73270 | HP-1 A | 2511070 |
| 72045 | LP A/B | 2511919 |
| 71468 | LL-2 AB | 2513227 | ii) Recipe for Formulation of the Samples:

Frozen concentrate cultures were thawed and mixed with the different amounts of a Glucidex 12 solution to a final formulation of 3.5% to 10.1% (W/W).

The different formulations are listed in Table 6.

iii) Measurement of Tm':

The samples were prepared in 100 µL alumina crucibles. The phase transition curves were recorded on the Mettlet DSC for all the formulations. The samples were inserted to the DSC at −90° C. Scanning temperature program: 7° C./min. −100° C.-0° C.

iv) Visual Evaluation of Melting Point of F-DVS R604.

The formulations were pellet-frozen in liquid nitrogen and 100 individual pellets (around 20-30 g) of pellets were poured into petridishes, thus forming a thin layer of loose single pellets. One sample of each of the formulations was placed at −46° C. After 14 days of storage the samples were examined to see if they were still loose or if the pellets had made clumps or seemed sticky—and if so—their willingness to be shaken into loose particles again.

Results:

Results of adding maltodextrine (Glucidex 12) to different cultures in various amounts are shown in FIG. 1. It is clear that increasing the concentration of maltodextrine increases Tm'. In Table 2 the results on evaluating the stickiness/clumping are listed. Samples with a Tm' above the storage temperature of −46° were loose pellets where as the samples having Tm' below −46° C. were sticking together.

TABLE 6

Formulations of samples, Initial melting temperature (Tm') and visual inspection of frozen pellets.

| Sample | Maltodextrin % | Tm' | Stored at minus 46° C. |
|---|---|---|---|
| HP B | 4.0 | −46 | − |
| H P B | 6.6 | −40 | +++ |
| HP B | 10.1 | −35 | +++ |
| HPA | 3.5 | −56 | − |
| HPA | 6.5 | −53 | − |
| HPA | 10.0 | −49 | − |
| HP-1 A | 6.0 | −57 | − |
| HPS A | 0.0 | −58 | not measured |
| HPS A | 6.1 | −53 | − |
| LP B | 6.0 | −45 | +++ |
| LP A | 0.0 | −60 | not measured |
| LP A | 6.0 | −54 | − |
| LL-2 B | 6.1 | −42 | +++ |
| LL-2 A | 0.0 | −61 | not measured |
| LL-2 A | 6.1 | −54 | − |

Note to table:
− designates clumped, caked or sticky (less than 20 of the 100 individual pellets remain as loose individual single pellets).
+++ designates Loose particles (at least 90 of the 100 individual pellets remain as loose individual single pellets).

Figure 2:
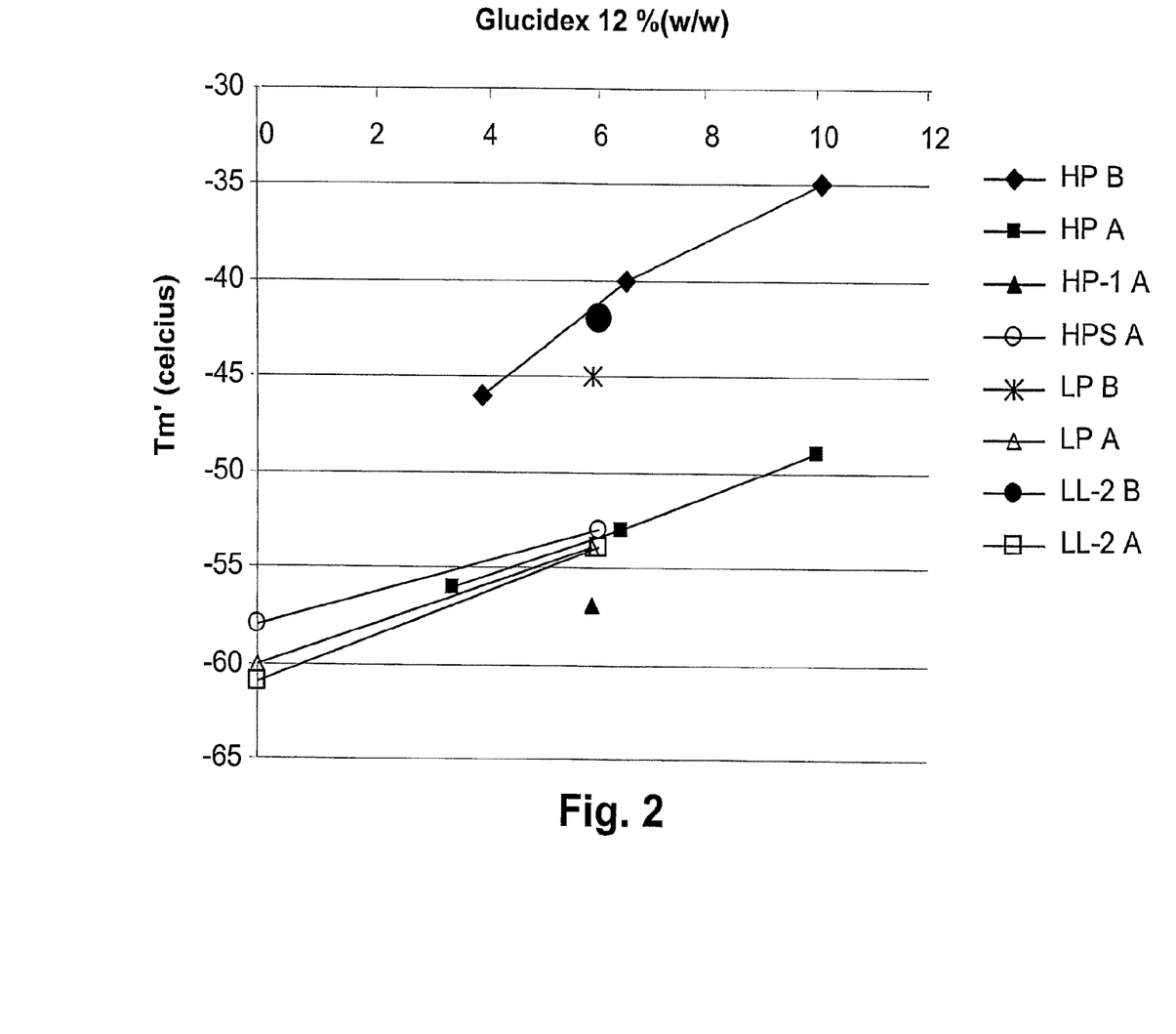
FIG. 2: Temperature of onset of ice melting (Tm') (Y-axis) of a number of cultures as a function of the maltodexdrin (Glucidex 12) concentration (% w/w) (X-axis). Culture name followed by "A" indicates that glycerine has been added to the culture, B indicates that glycerine was not added to the culture before pellet freezing.

The result is illustrated in table 6 and in FIG. 2 and shows that maltodextrin is an effective agent to increase the Tm' in cultures containing 10% v/v glycerine (A-series) as well in cultures not containing glycerine (B-series). This experiment further demonstrates that a well known cryoprotectant (i.e. glycerine) not can be used to increase the physical stability during storage of a pellet-frozen culture.

REFERENCES

Cárcoba, R. et al. "Influence of cryoprotectants on the viability and acidifying activity of frozen and freeze-dried cells of the novel starter strain *Lactococcus lactis* subsp. *lactis* CECT 5180*", Eur Food Res Technol* (2000) 211, 433-437

Chavarri, F. J. et al, "Cryoprotective agents for frozen concentrated starters from non-bitter *Streptococcus Lactis* strains", *Biotechnology letters*, vol 10, 1, 11-16 (1988)

DE2805676, (Jespersen et al.), 18 Aug. 1978.

Fennema O. R. (ed.) Food Chemistry, 3. ed. Marcel Dekker, 1067 pp. (ISBN: 0-8247-9346-3), 1996.

FR2393251, (Jespersen et al.), 29 Dec. 1978.

IDF (1998), International IDF Standard 146A:1998 "Identification of Characteristic Microorganisms".

Roos, Y. and M. Karel (1991) Phase transitions of amorphous sucrose and frozen sucrose solutions. J. Food Science, 56:266-267.

ROOS, Y. Phase Transition in Foods. ACADEMIC PRESS, New York, USA. 360 pp., (ISBN: 0-12-595340-2), 1995.
U.S. Pat. No. 4,140,800 (Leo Kline) 20 Feb. 1979. WO 00/39281 (Kringelum et al.) 6 Jul. 2000.
WO 2004/065584 A1 (Bisgaard-Frantzen et al.) 5 Aug. 2004 (similar to International Application Number PCT/DK2004/000025)

We claim:

1. A stable pellet-frozen lactic acid bacterial culture in the form of individual pellets comprising:
   (a) a lactic acid bacterial culture; and
   (b) at least one additive compound, which increases the Tm' value of the frozen lactic acid bacteria culture from a range between about −70° C. and −46° C. to a range between about −45° C. and about −15° C., wherein the additive compound is selected from the group consisting of cyclodextrin, maltitol, trehalose, fish gelatin, maltodextrin, spray gum, inosine-5'-monophosphate, and inosine and wherein:
      (i) the pellet-frozen culture has a weight of at least 50 g frozen material and a content of viable bacteria of at least $10^9$ colony forming units per g frozen material, and
      (ii) the additive compound in the culture is in an amount of from 0.5% to 13% of frozen material.

2. The pellet-frozen culture of claim 1, wherein the lactic acid bacterium is capable of utilizing sucrose.

3. The pellet-frozen culture of claim 1, wherein the lactic acid bacterium is not capable of utilizing sucrose.

4. The pellet-frozen culture of claim 1, wherein the lactic acid bacterium is selected from the group consisting of *Bifidobacterium* spp., *Brevibacterium* spp., *Propionibacterium* spp., *Lactococcus* spp., *Lactobacillus* spp., *Streptococcus* spp., *Enterococcus* spp., *Pediococcus* spp., *Leuconostoc* spp., *Oenococcus* spp., fungal spp., and a mixture thereof.

5. The pellet-frozen culture of claim 4, wherein the *Lactococcus* spp, comprises *Lactococcus lactis* subsp, *lactis* and *Lactococcus lactis* subsp, *cremoris*.

6. The pellet-frozen culture of claim 4, wherein the *Lactobacillus* spp, comprises *Lactobacillus acidophilus*.

7. The pellet-frozen culture of claim 4, wherein the fungal spp, comprises *Pencillium* spp., *Cryptococcus* spp., *Debraryomyces* spp., *Klyveromyces* spp, and *Saccharomyces* spp.

8. The pellet-frozen culture of claim 1, wherein the lactic acid bacterium is selected from the group consisting of *Lactococcus* species, *Streptococcus* species, *Enterococcus* species, *Lactobacillus* species, *Leuconostoc* species and *Pediococcus* species, and a mixture thereof.

9. The pellet-frozen culture of claim 1, wherein the lactic acid bacterium is a mesophilic bacterium.

10. The pellet-frozen culture of claim 1, wherein the Tm' is increased to a range between about −43° C. and about −15° C.

11. The pellet-frozen culture of claim 1, wherein the Tm' is increased to a range between about −39° C. and about −15° C.

12. The pellet-frozen culture of claim 1, wherein the additive compound has a molecular weight of between about 150 g/mol and about 100000 g/mol.

13. The pellet-frozen culture of claim 1, wherein the additive compound increases the viability of the culture.

14. The pellet-frozen culture of claim 1, further comprising a cryoprotective agent.

15. The pellet-frozen culture of claim 14, wherein the cryoprotective agent is a protein or a protein hydrolysate.

16. The pellet-frozen culture of claim 15, wherein the cryoprotective agent is selected from the group consisting of malt extract, skimmed milk powder, whey powder, yeast extract, gluten, collagen, gelatin, elastin, keratin, and albumins.

17. The pellet-frozen culture of claim 14, wherein the cryoprotective agent is a carbohydrate.

18. The pellet-frozen culture of claim 17, wherein the cryoprotective agent is selected from the group consisting of a pentose, a hexose, a disaccharide, an oligosaccharide, an oligofrutose, a polysaccharide, and a sugar alcohol.

19. The pellet-frozen culture of claim 14, wherein the cryoprotective agent is a compound involved in biosynthesis of nucleic acids.

20. The pellet-frozen culture of claim 1, wherein the additive compound is in an amount selected from the group consisting of between 1% and 12%, between 2% and 10%, and between 5% and 10% of frozen material.

21. The pellet-frozen culture of claim 1, wherein the culture remains in the form individual pellets upon storage at about −46° C. for at least 7 to 14 days.

22. A method for making a stable pellet-frozen lactic acid bacterial culture in the form of individual pellets, comprising:
    (a) adding at least one additive compound, which is capable of increasing the Tm' value of the frozen lactic acid bacteria culture from a range between about −70° C. and −46° C. to a range between about −45° C. and about −15° C., to a liquid lactic acid bacterial culture, wherein the additive compound is selected from the group consisting of cyclodextrin, maltitol, trehalose, fish gelatin, maltodextrin, spray gum, inosine-5'-monophosphate, and inosine; and
    (b) freezing the liquid culture to obtain a pellet-frozen culture, wherein:
       (i) the pellet-frozen culture has a weight of at least 50 g frozen material and a content of at least $10^9$ colony forming units per g of frozen material; and
       (ii) the additive compound in the culture is in an amount of from 0.5% to 13% of frozen material.

23. The method of claim 22, further comprising packing the pellet-frozen culture.

24. The method of claim 22, wherein the lactic acid bacterium is selected from the group consisting of *Bifidobacterium* spp., *Brevibacterium* spp., *Propionibacterium* spp., *Lactococcus* spp., *Lactobacillus* spp., *Streptococcus* spp., *Enterococcus* spp., *Pediococcus* spp., *Leuconostoc* spp., *Oenococcus* spp., fungal spp., and a mixture thereof.

25. The method of claim 22, wherein the lactic acid bacterium is selected from the group consisting of *Lactococcus* species, *Streptococcus* species, *Enterococcus* species, *Lactobacillus* species, *Leuconostoc* species and *Pediococcus* species, and a mixture thereof.

* * * * *